United States Patent
Castañeda et al.

(10) Patent No.: US 12,038,624 B2
(45) Date of Patent: Jul. 16, 2024

(54) EYEWEAR HAVING BIOMETRIC SENSING

(71) Applicants: Julio Cesar Castañeda, Redondo Beach, CA (US); Rajeev Ramanath, Torrence, CA (US)

(72) Inventors: Julio Cesar Castañeda, Redondo Beach, CA (US); Rajeev Ramanath, Torrence, CA (US)

(73) Assignee: Snap Inc., Santa Monica, CA (US)

(*) Notice: Subject to any disclaimer, the term of this patent is extended or adjusted under 35 U.S.C. 154(b) by 159 days.

(21) Appl. No.: 17/408,760

(22) Filed: Aug. 23, 2021

(65) Prior Publication Data

US 2021/0382322 A1 Dec. 9, 2021

Related U.S. Application Data

(63) Continuation of application No. 16/263,034, filed on Jan. 31, 2019, now Pat. No. 11,137,620.

(60) Provisional application No. 62/634,273, filed on Feb. 23, 2018.

(51) Int. Cl.
| | |
|---|---|
| G02C 5/02 | (2006.01) |
| A61B 5/021 | (2006.01) |
| A61B 5/024 | (2006.01) |
| G02C 5/12 | (2006.01) |
| G02C 11/00 | (2006.01) |

(Continued)

(52) U.S. Cl.
CPC .............. *G02C 5/02* (2013.01); *A61B 5/021* (2013.01); *A61B 5/024* (2013.01); *G02C 5/12* (2013.01); *G02C 11/10* (2013.01); *H05K 1/189* (2013.01); *G02C 5/143* (2013.01)

(58) Field of Classification Search
None
See application file for complete search history.

(56) References Cited

U.S. PATENT DOCUMENTS

| 7,648,463 B1 | 1/2010 | Elhag et al. |
| 7,771,046 B2 | 8/2010 | Howell et al. |
| 10,401,956 B2 * | 9/2019 | Price ............ G01J 1/044 |

(Continued)

FOREIGN PATENT DOCUMENTS

| CN | 101046557 A | 10/2007 |
| CN | 104905780 A | 9/2015 |

(Continued)

OTHER PUBLICATIONS

International Search Report and Written Opinion for International Application No. PCT/US2019/015937, dated Apr. 5, 2019 (Apr. 5, 2019)—10 pages.

*Primary Examiner* — Christopher Stanford
*Assistant Examiner* — Journey F Sumlar
(74) *Attorney, Agent, or Firm* — Culhane PLLC; Stephen J. Weed

(57) ABSTRACT

In an example, the eyewear includes an optical element, electronic components, and a support structure configured to support the optical element and the electronic components. The support structure defines a region for receiving at least a portion of a head of a user. The eyewear also includes a biometric sensor coupled to the electronic components and supported by the support structure. The biometric sensor is attached to the support structure and positioned to detect, in the region, a biometric signal representative of a biometric of the user for processing by the electronic components.

20 Claims, 10 Drawing Sheets

(51) Int. Cl.
*H05K 1/18* (2006.01)
*G02C 5/14* (2006.01)

(56) References Cited

U.S. PATENT DOCUMENTS

| | | |
|---|---|---|
| 11,137,620 B2 | 10/2021 | Castañeda et al. |
| 2012/0127420 A1 | 5/2012 | Blum et al. |
| 2014/0204334 A1 | 7/2014 | Stoll |
| 2015/0189724 A1 | 7/2015 | Karc et al. |
| 2015/0347764 A1* | 12/2015 | Cornell .................. G06F 21/32 726/28 |
| 2016/0367189 A1 | 12/2016 | Aimone et al. |
| 2017/0056679 A1 | 3/2017 | Peterson et al. |
| 2018/0092706 A1* | 4/2018 | Anderson ............. G06T 19/006 |

FOREIGN PATENT DOCUMENTS

| | | |
|---|---|---|
| CN | 105380608 A | 3/2016 |
| CN | 106343972 A | 1/2017 |
| WO | 2017042824 A1 | 3/2017 |
| WO | 2017118594 A1 | 7/2017 |
| WO | 2017196294 A1 | 11/2017 |

* cited by examiner

EYEWEAR HAVING BIOMETRIC SENSING

CROSS-REFERENCE TO RELATED APPLICATIONS

The present application is a continuation of U.S. patent application Ser. No. 16/263,034 filed Jan. 31, 2019, and claims priority to U.S. Provisional Patent Application No. 62/634,273 filed on Feb. 23, 2018, the contents of both of which are incorporated fully herein by reference.

FIELD

The subject matter disclosed herein generally relates to eyewear and, more particularly, to eyewear that senses biometrics of the eyewear user.

BACKGROUND

Biometrics include physical characteristics/measurements of an individual such as heart rate, blood pressure, blood oxygen level, etc. Biometrics are useful in determining the health and wellness of an individual. Accordingly, convenient methods and apparatus for sensing biometric parameters are useful.

DETAILED DESCRIPTION

Figure 1A:
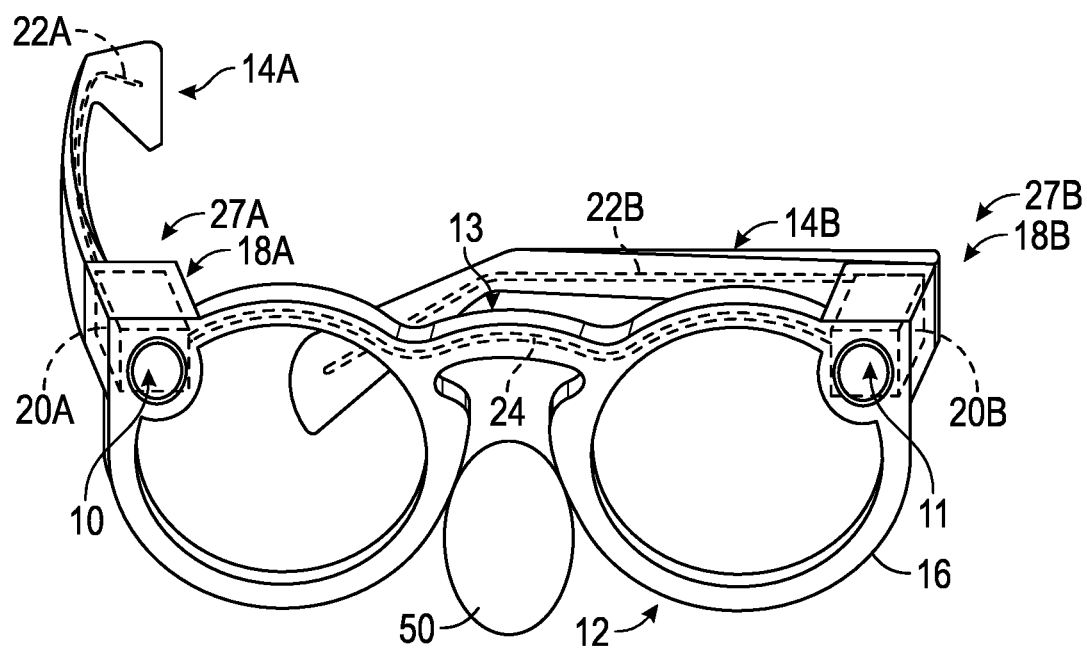
FIG. 1A is a perspective view of an eyewear example including electronic components and a support structure supporting the electronic components.

In the following detailed description, numerous specific details are set forth by way of examples in order to provide a thorough understanding of the relevant teachings. However, it should be apparent to those skilled in the art that practice of the present teachings is possible without such details. In other instances, we describe well known methods, procedures, components, and circuitry at a relatively high-level, without detail, in order to avoid unnecessarily obscuring aspects of the present teachings.

The term "coupled" as used herein refers to any logical, optical, physical, or electrical connection, link, or the like by which signals or light produced or supplied by one system element are imparted to another coupled element. Unless described otherwise, coupled elements or devices are not necessarily directly connected to one another and may be separated by intermediate components, elements or communication media that may modify, manipulate, or carry the light or signals.

The orientations of the eyewear, associated components and any devices incorporating a biometric sensor such as shown in any of the drawings, are given by way of example only, for illustration and discussion purposes. In operation, the eyewear may be oriented in directions suitable to the particular application of the eyewear, for example up, down, sideways, or other orientation. Also, to the extent used herein, any directional term, such as front, rear, inwards, outwards, towards, left, right, lateral, longitudinal, up, down, upper, lower, top, bottom and side, are by way of example only, and are not limiting as to direction or orientation.

In an example, the eyewear includes an optical element, electronic components, and a support structure configured to support the optical element and the electronic components. The support structure defines a region for receiving at least a portion of a head of a user. The eyewear also includes a biometric sensor coupled to the electronic components and supported by the support structure. The biometric sensor is attached to the support structure and is positioned to detect, in the region, a biometric signal representative of a biometric of the user for processing by the electronic components.

In an example, electronic components control the eyewear based on a method to detect a biometric signal of a user. The method includes triggering, by electronic components in the eyewear, a biometric sensor in the eyewear to detect a biometric signal representative of a biometric of the user. The method also includes processing, by the electronic components, the biometric signal to determine the biometric of the user.

Biometrics are measurable physical characteristics of a person. The medical industry uses biometrics to monitor physical characteristics of patients. Consumers use dedicated biometric devices to monitor their health. Biometrics include but are not limited to heart rate, blood pressure, oxygen levels in blood, electrical activity of anatomy (heart, brain, etc.). This disclosure describes eyewear that measures biometrics using various sensors positioned on the eyewear. As used herein, the term "eyewear" refers to any smart optical device having a support structure worn by a user including but not limited to smart glasses, smart goggles, and display screens.

FIG. 1A depicts a front perspective view of example eyewear 12 for measuring biometrics. The illustrated eyewear 12 includes a support structure 13 that has temples 14A and 14B and a frame 16. Eyewear 12 additionally includes articulated joints 18A and 18B, electronic components 20A and 20B, and core wires 22A, 22B and 24.

Support structure 13 supports one or more optical elements within a field of view of a user when worn by the user. For example, frame 16 supports the one or more optical elements. As used herein, the term "optical elements" refers to lenses, transparent pieces of glass or plastic, projectors, screens, displays and other devices for presenting visual images or through which a user perceives the visual images. In an embodiment, respective temples 14A and 14B connect to frame 16 at respective articulated joints 18A and 18B. The illustrated temples 14A and 14B are elongate members having core wires 22A and 22B extending longitudinally therein.

Temple 14A is illustrated in a wearable condition and temple 14B is illustrated in a collapsed condition in FIG. 1A. As shown in FIG. 1A, articulated joint 18A connects temple 14A to a right end portion 27A of frame 16. Similarly, articulated joint 18B connects temple 14B to a left end portion 27B of frame 16. The right end portion 27A of frame 16 includes a housing that carries the electronic components 20A therein, and left end portion 27B includes a housing that carries electronic components 20B therein.

A plastic material or other material embeds core wire 22A along with an outer cap of temple 14A. The core wire 22A extends longitudinally from adjacent articulated joint 18A toward a second longitudinal end of temple 14A. Similarly, a plastic material or other material embeds core wire 22B along with an outer cap of temple 14B. Core wire 22B extends longitudinally from adjacent articulated joint 18B toward a second longitudinal end of temple 14B. Core wire 24 extends from the right end portion (terminating adjacent electronic components 20A) to the left end portion 27B (terminating adjacent electronic components 20B).

Support structure 13 (e.g., either or both of temple(s) 14A, 14B and/or frame 16) carries electronic components 20A and 20B. Electronic components 20A and 20B include a power source, power and communication related circuitry, communication devices, display devices, a computer, a memory, modules, and/or the like (not shown). Electronic components 20A and 20B may also include a camera/microphone 10 for capturing images and/or videos, and indicator LEDs 11 indicating the operational state of eyewear 12.

In one example, temples 14A and 14B and frame 16 are constructed of a plastics material, cellulosic plastic (e.g., cellulosic acetate), an eco-plastic material, a thermoplastic material, or the like in addition to core wires 22A, 22B and 24 embedded therein. Core wires 22A, 22B and 24 provide structural integrity to support structure 13 (i.e., temple(s) 14A, 14B and/or frame 16). Additionally, core wires 22A, 22B and/or 24 act as a heat sink to transfer heat generated by electronic components 20A and 20B away therefrom to reduce the likelihood of localized heating adjacent electronic components 20A and 20B. As such, core wires 22A, 22B and/or 24 thermally couple the electronic components to the heat source to provide a heat sink for the heat source. Core wires 22A and 22B and/or 24 are constructed of a relatively flexible conductive metal or metal alloy material such as one or more of an aluminum, an alloy of aluminum, alloys of nickel-silver, and a stainless steel, for example.

Figure 1B:
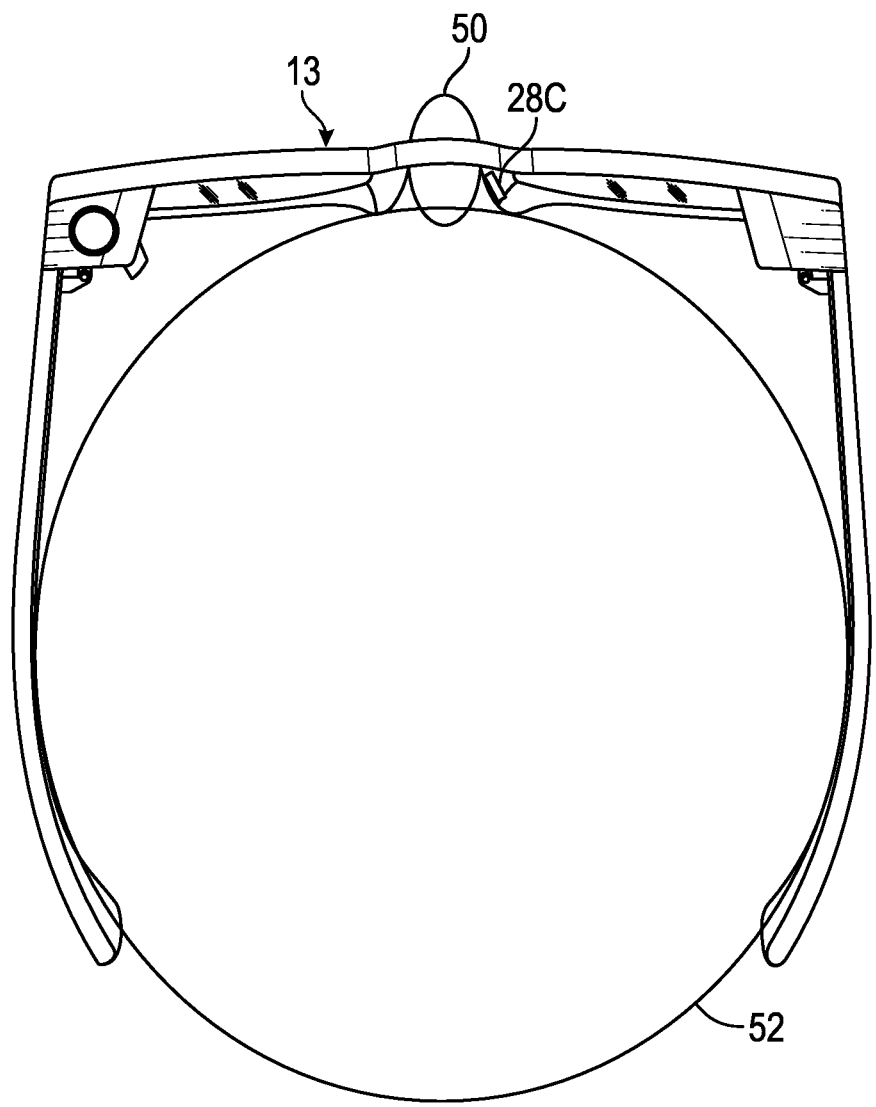
FIG. 1B is a top view of the eyewear example of FIG. 1A illustrating a region defined by the eyewear for receiving a head of a user wearing the eyewear.

The support structure 13 defines a region 50 that receives at least a portion of the head of the user (e.g., the nose) when the eyewear 12 is worn. As illustrated in FIG. 1B, the support structure 13 may define other regions (e.g., region 52 defined by the frame 12 and temples 14A and 14B) for receiving another portion (e.g., the main portion) of the head of the user. The defined region(s) are one or more regions containing at least a portion of the head of a user that are encompassed by, surrounded by, adjacent, and/or near the support structure when the user is wearing the eyewear 12. Eyewear 12 also includes one or more biometric sensors (e.g., biometric sensor 28C). Described below are details of the type and placement of the biometric sensor(s).

Figure 1C:
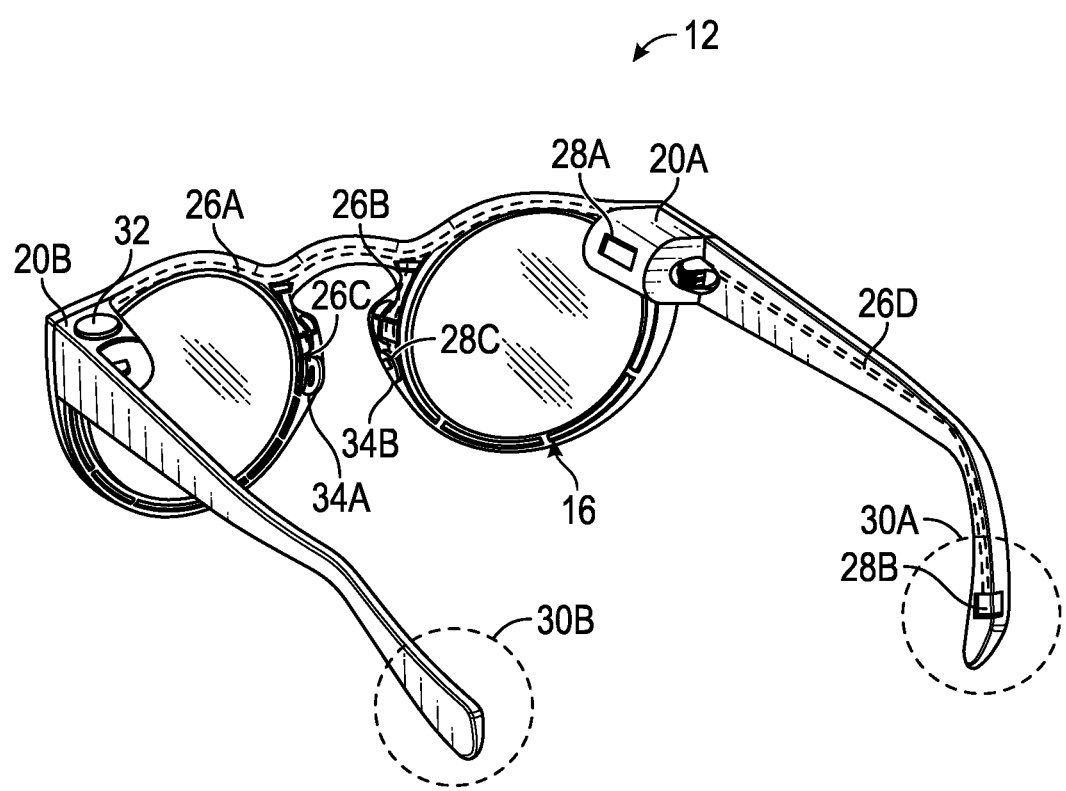
FIG. 1C is another perspective view of the eyewear example of FIG. 1A.

FIG. 1C depicts another perspective view of eyewear 12 with a transparent frame 16 for illustration purposes. Eyewear 12 includes electronics 20A and 20B (e.g., camera, microphone, LEDs, wireless transceiver, etc.). In addition, eyewear 12 includes biometric sensors (e.g., biometric sensors 28A, 28B and 28C) installed at one or more locations throughout frame 16 and/or temples 14A and/or 14B. For example, biometric sensors may be installed in at least one of nose pads 34A or 34B (see sensor 28C), the housing of electronics 20A (see sensor 28A), temple areas 30A and 30B (see sensor 28B), etc. These biometric sensors may include light transceivers, probes with electrodes, or the like, and electrically couple to electronics 20A and 20B (e.g., through one or more flexible printed circuit boards (FPCBs)).

FPCBs, as shown in FIG. 1C, extend through various portions of frame 16 and temples 14A and 14B to electrically connect these electronics 20A and 20B to the biometric sensors. For example, as shown in FIG. 1C, FPCB 26A (primary FPCB) extends through frame 16 to couple electronics 20A and 20B together. Other FPCBs (secondary FPCB) may extend through the frame and temples. For example, secondary FPCBs 26B and 26C extend from main FPCB 26A to biometric sensor 28C embedded into nose pad 34B. In another example, FPCB 26D extends from electronics 20A to biometric sensor 28B embedded into temple area 30A. Although not shown, another FPCB extends from electronics 20B to a biometric sensor (not shown) embedded into temple area 30B. The use of secondary FPCBs enables embedding of other electronic devices (e.g., biometric sensors and the like) at various locations throughout the support structure of eyewear 12. When the user wears eyewear 12, the biometric sensors are located at a position to provide a way for detecting a biometric signal (e.g., heart rate, blood pressure, etc.) of the user.

FPCBs 26A, 26B, 26C and 26D shown in FIG. 1C include one or more electrical traces for routing electrical signals between the electronic components and the biometric sensors. These FPCBs embed in the frame and temples of eyewear 12 during the manufacturing process. For example, a first shot of a two-shot molding process injects plastic into a mold to form the front half of frame 16 and/or temple 14A. After forming the front halves, the FPCBs, along with any electronic components (e.g., the biometric sensors) insert within the mold at locations with respect to the front halves. A second shot of the two-shot molding process injects more plastic into the mold to cover the components and form the back half of frame 16 or temple 14A such that the front and back halves of frame 16 and/or temple 14A envelope the FPCBs and electronics. After molding the frame and both temples, they are mechanically connected together (e.g., with screws) to form the eyewear 12.

Embedding biometric sensors into frame 16 and/or temples 14A and 14B enables eyewear 12 to detect biometric signals of the user. To accomplish this feature, various locations on frame 16 and/or temples 14A and 14B provide support for various types of biometric sensors.

Figure 1D:
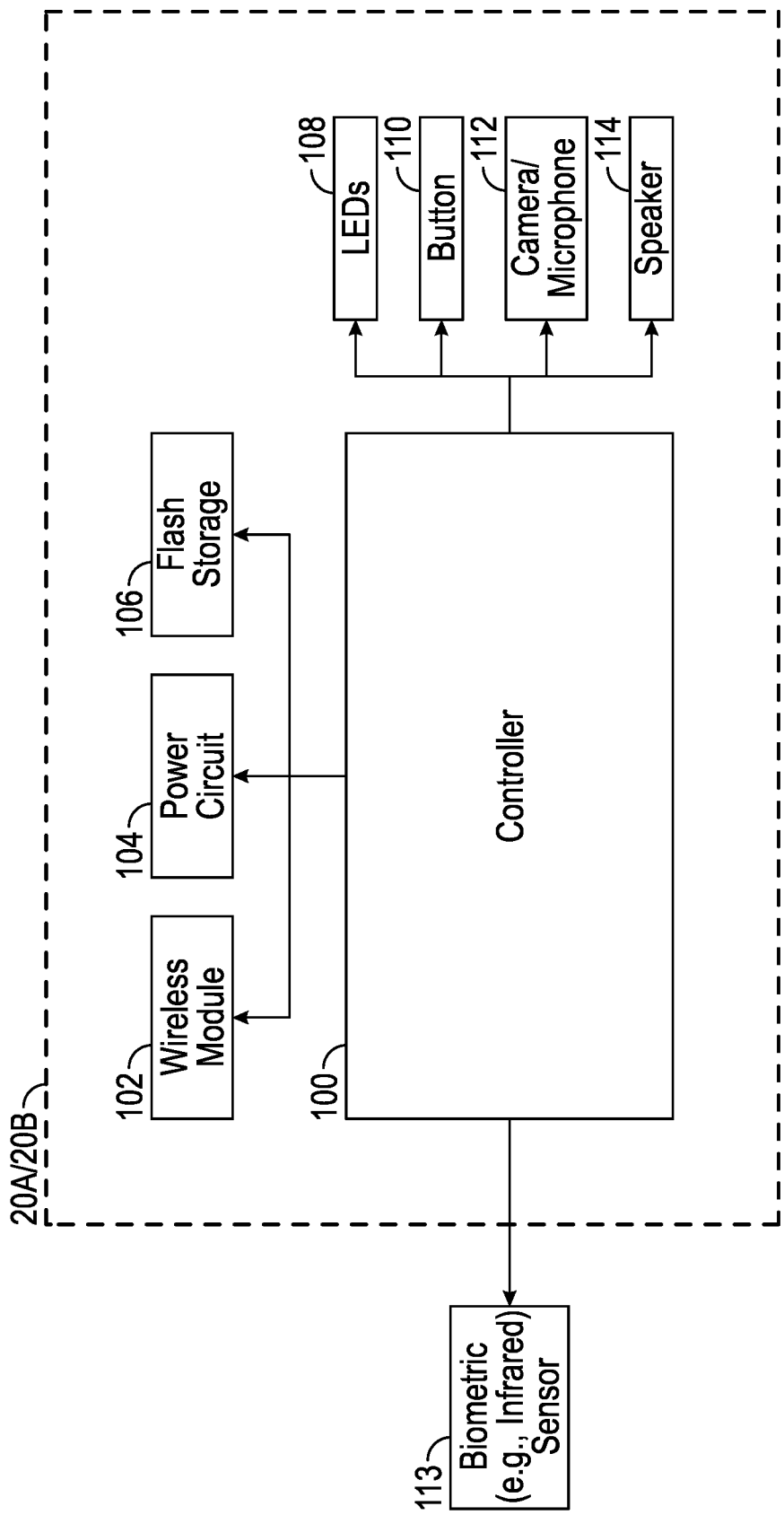
FIG. 1D is a block diagram of an example of the electronic components supported by the eyewear example of FIG. 1A.

FIG. 1D is a block diagram of example electronic components 20A and 20B connected to a biometric sensor 113. The illustrated electronic components 20A and 20B include controller 100 (e.g., lower power processor, image processor, etc.) for controlling the various devices in eyewear 12, wireless module (e.g., Bluetooth™) 102 for facilitating communication between eyewear 12 and a client device (e.g., smartphone not shown), and power circuit 104 (e.g., battery, filter, etc.) for powering eyewear 12. Electronic components 20A and 20B also include flash storage 106 for storing data (e.g., images, video, image processing software, etc.), LEDs 108 (e.g. colored LEDs) for providing visual information (e.g., indicators) to the user, button 110 (e.g., momentary push button) for triggering eyewear 12 to capture images/video, camera/microphone 112 for capturing images/video and sound, a speaker 114 for providing audible information (e.g., indicators) to the user and a biometric sensor 113 (e.g., IR sensor).

Wireless module 102 may connect with a client device such as a smartphone, tablet, phablet, laptop computer, desktop computer, networked appliance, access point device, or any other such device capable of connecting with wireless module 102. These connections may be implemented, for example, using one or more of Bluetooth, Bluetooth LE, Wi-Fi, Wi-Fi direct, a cellular modem, and a near field communication system, as well as multiple instances of any of these systems. Communication may include transferring software updates, images, videos, sound between eyewear 12 and the client device (e.g., images captured by eyewear 12 may be uploaded to a smartphone).

Camera/microphone 112 for capturing the images/video may include digital camera elements such as a charge-coupled device, a lens, or any other light capturing elements used to capture image data. Camera/microphone 112 includes a microphone having a transducer for converting sound into an electrical signal.

Button 110 may be a physical button (e.g., button 32 in FIG. 1B) that, when depressed, sends a user input signal to controller 100. Pressing button 110 for a predetermined period of time (e.g., three seconds) may be processed by controller 100 as a request to turn on eyewear 12 (e.g., transition eyewear 12 from an off or sleep mode of operation to a low power mode of operation).

Controller 100 controls the electronic components. Controller 100 includes circuitry to receive signals from camera 112 and process those signals into a format suitable for storage in memory 106. Controller 100 powers on and boots to operate in a normal operational mode, or to enter a sleep mode. Depending on various power design elements controller 100 may consume a small amount of power even when it is in an off state and/or a sleep state. This power, however, is negligible compared to the power used by controller 100 when it is in an on state, and has a negligible impact on battery life.

In one example, controller 100 includes a microprocessor integrated circuit (IC) customized for processing sensor data from camera 112, along with volatile memory used by the microprocessor to operate. The memory may store software code for execution by controller 100.

Each of the electronic components require power to operate. Power circuit 104, e.g., a battery, power converter, and distribution circuitry (not shown), may provide the power to operate the electronic components. The battery may be a rechargeable battery such as lithium-ion or the like. Power converter and distribution circuitry may include electrical components for filtering and/or converting voltages for powering the various electronic components.

LEDs 108, among other uses, are indicators on eyewear 12 to indicate a number of functions. For example, LEDs 108 may illuminate each time the user presses button 110 to indicate that eyewear 12 is recording images and/or video and/or sound. These LEDs may be located at location 20B as shown in FIG. 1A.

In addition to the electronic components described above, controller 100 also couples to biometric sensor 113. Biometric sensor 113 connects to controller 100 for monitoring/sensing a biometric signal from the user's head when the user is wearing eyewear 12. Biometric sensor 113 senses the biometric signal of the user, converts the biometric signal to a representative electrical signal, and relays this electrical signal to controller 100.

Biometric sensor 113 are located at one or more locations (nose pad, frame, temple, etc.) on eyewear 12 for sensing a biometric signal of the user's head. Controller 100 of the eyewear 12 may automatically control the operation of biometric sensor 113 to detect the biometric signal. For example, eyewear 12 may use biometric sensor 113 to detect blood flow in the user's nose. In this example, biometric sensor 113 (positioned in the nose pad of eyewear 12) may be an infrared (IR) transceiver configured to transmit IR light towards the user's nose and receive a reflected IR signal. When wearing eyewear 12, the user's nose reflects the transmitted IR light, based at least in part on the amount of blood flow through the user's nose. During a heartbeat, when the heart contracts, it pumps blood through arteries increasing blood pressure in the nose. In between heartbeats, the blood pressure in the nose decreases. The amount of blood pressure in the nose affects the amount of IR light reflected. Therefore, the blood flow through the nose amplitude modulates the reflected light. For example, the intensity of the reflected light increases during the heartbeat, and decreases between heartbeats. This reflected light is received and converted (e.g., by a photo-resistor in biometric sensor 113) into a corresponding electrical signal having peaks and valleys correlated to the heart rhythm. Controller 100 or a personal computing device (e.g., smartphone) receives and analyzes this electrical signal to determine one or more biometrics (e.g., heart rate, blood pressure, etc.).

Wires, PCBs and FPCBs positioned throughout the eyewear implement the various electrical connections between controller 100 and the other electronic components including the biometric sensors shown in FIG. 1D. These electrical connections extend through various portions of frame 16 and/or temples 14A and 14B.

Figure 2:
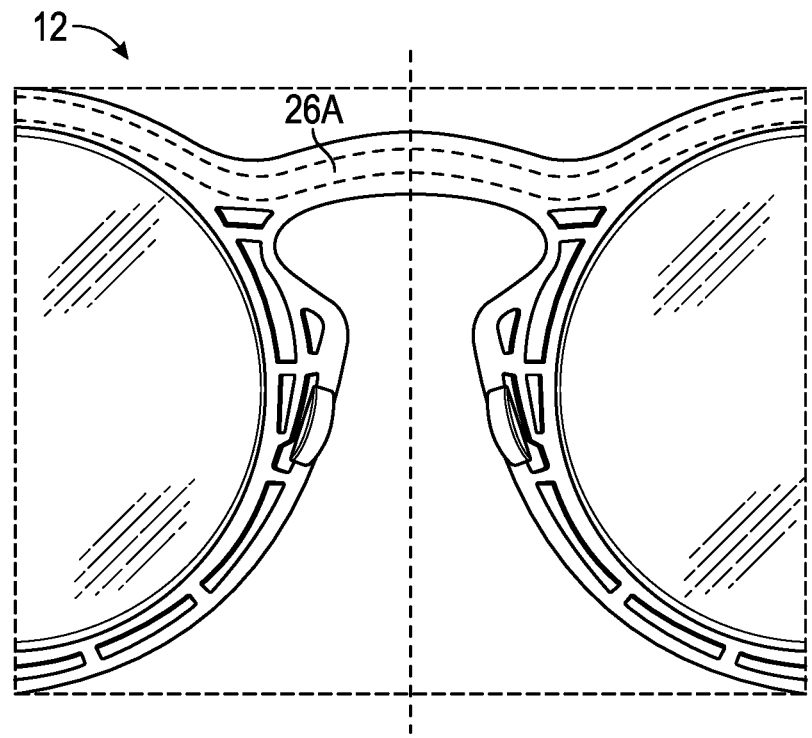
FIG. 2 is a close-up partial view of the frame of the eyewear example of FIG. 1A depicting a flexible printed circuit board routed through the frame.

FIG. 2 is a close-up partial view of eyewear 12 in FIG. 1C showing FPCB 26A routed through the frame. FPCB 26A is the primary FPCB in eyewear 12, and electrically connects electronics 20A with electronics 20B. Secondary FPCBs (not shown) support electrical connections to biometric sensors 113 located at one or more locations in support structure 13 of eyewear 12.

Figure 3:
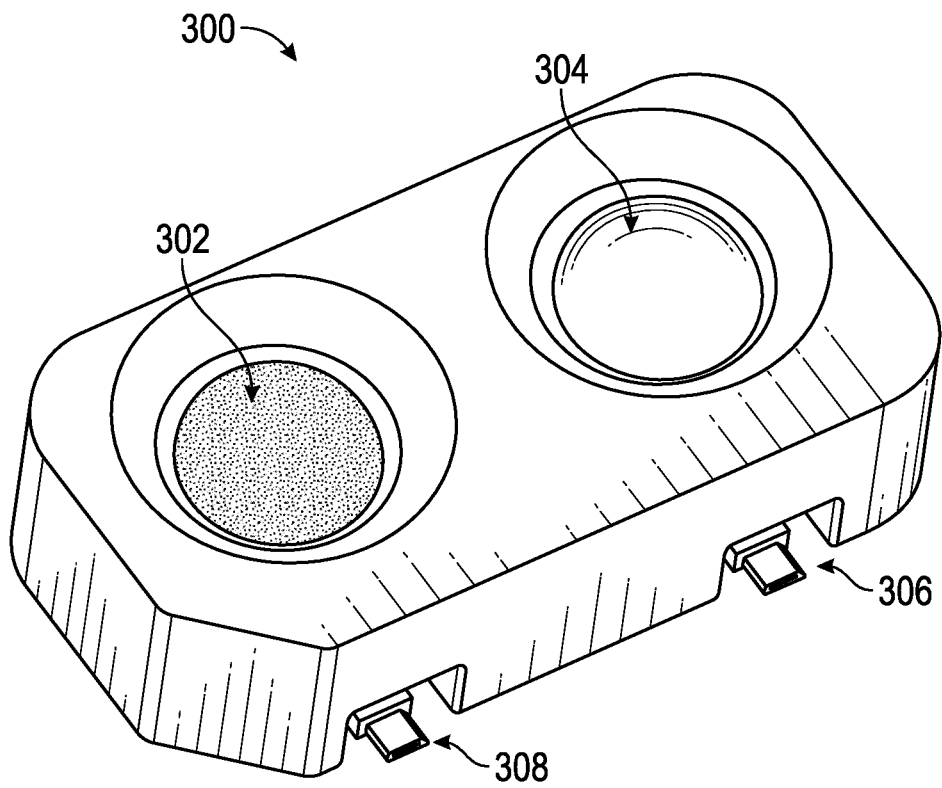
FIG. 3 is a perspective view of biometric sensor example.

An example of one type of biometric sensor 113 (FIG. 1D) is shown in FIG. 3. The illustrated biometric sensor is an infrared (IR) transceiver 300 including an IR transmitter 304, IR receiver 302, and electrical terminals 306/308. During operation, IR transceiver 300 emits an IR signal from IR transmitter 304, senses a reflection of the transmitted IR signal (e.g., reflected by the user's skin) using receiver 302, and amplitude modulates an electrical signal representing the sensed reflection. In general, if no object is present in front of IR transmitter 304, then IR receiver receives no reflection. If an object is present, however, IR receiver 302 receives a reflection and generates an electrical signal.

For example, when biometric sensor 300 is oriented towards the user's nose, the user's nose reflects the transmitted IR light and the sensors receive the reflected IR light. The intensity of this reflected IR signal is dependent on the blood flow through the user's nose. When the user's heart pumps blood into the nose, the blood pressure in the nose rises. This increase in blood pressure reflects more IR light, and therefore IR transceiver 300 receives more reflected IR light. In between heartbeats, the blood pressure decreases, thereby reflecting less IR light. The blood flow through the user's nose thus effectively amplitude modulated the IR light during reflection for receipt by IR transceiver 300 which, in turn, amplitude modulates electrical current flowing through terminals 306/308. IR transceiver 300 then outputs this modulated current to controller 100 for further processing. For example, controller 100 may be a signal processor that analyzes the modulated current signal (e.g., measuring the period between signal peaks, measuring the amplitude of the signal peaks, etc.) to determine a biometric (e.g., heart rate, blood pressure, etc.).

Biometric sensor 113 (e.g., IR transceiver 300) may be positioned at various locations on eyewear 12. For example, as shown in FIGS. 4A and 4B, one or more nose pads of eyewear 12 may embed biometric sensor 113 to sense blood flow through the user's nose.

Figure 4A:
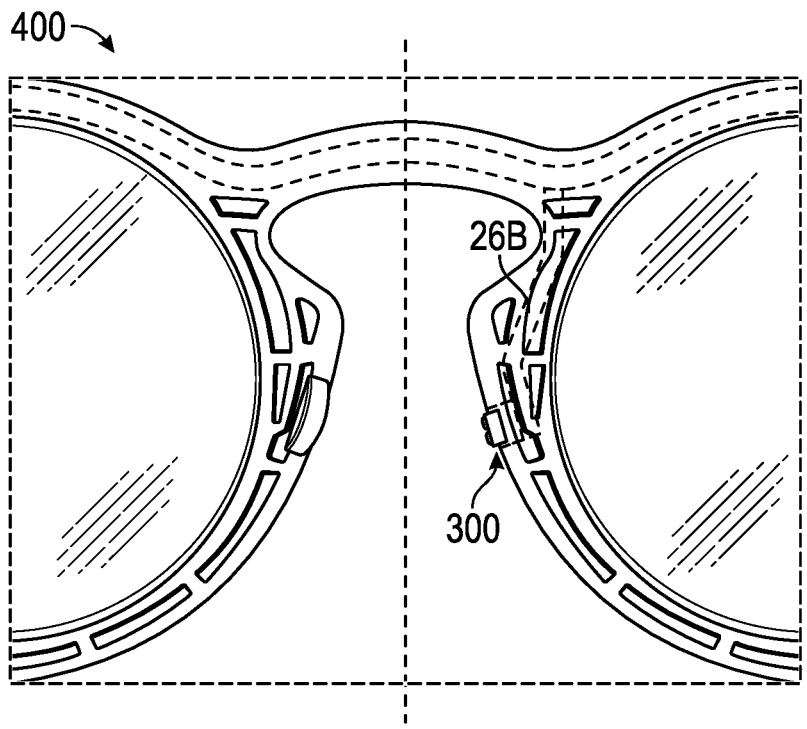
FIG. 4A is another close-up partial view of the eyewear example of FIG. 1A depicting a flexible printed circuit board routed to a biometric sensor located in a nose pad.
Figure 4B:
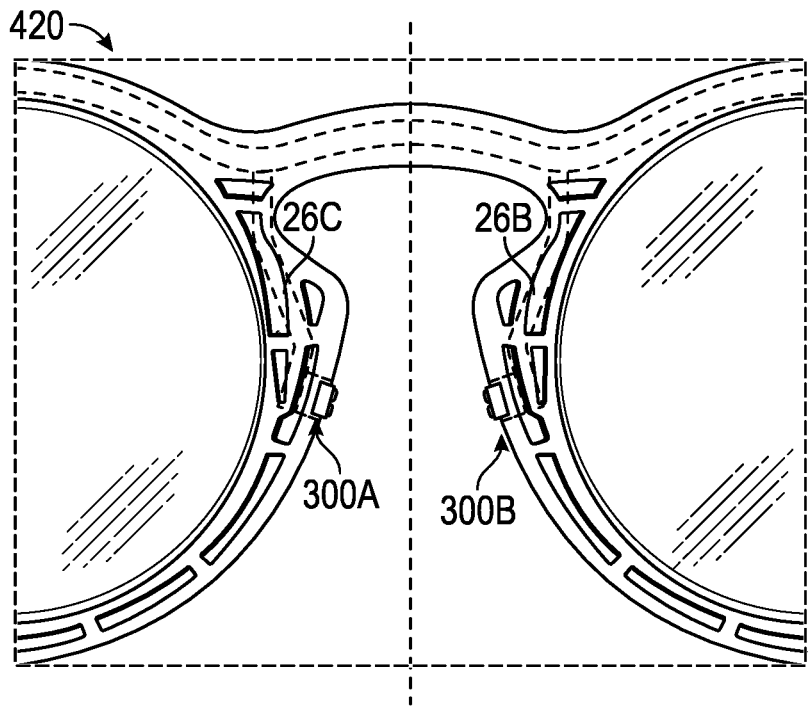
FIG. 4B is another close-up partial view of the eyewear example of FIG. 1A depicting a flexible printed circuit board routed to multiple biometric sensors located in the nose pads.

FIG. 4A depicts a close-up partial view 400 of eyewear 12 in FIG. 1A, where secondary FPCB 26B extends from main FPCB 26A to IR transceiver 300 positioned in one of the nose pads. As described above, IR transceiver 300 transmits IR light towards the user's nose and receives the reflected IR light to produce a corresponding electrical signal. Controller 100 may then analyze this electrical signal to determine a biometric of the user.

Eyewear 12 supports multiple biometric sensors. The biometric sensors may be the same or different. Additionally, the biometric sensors sense the same biometric or senses different biometrics. In an example, where the sensors are used to sense the same biometric, FIG. 4B depicts a close-up view 420 of eyewear 12 in FIG. 1C with biometric sensors 300A and 300B, respectively, positioned in each of the two nose pads. In this example, secondary FPCBs 26B and 26C both extend from primary FPCB 26A to respective biometric sensors 300A and 300B. Both biometric sensors 300A and 300B illuminate opposite sides of the user's nose, receive corresponding IR reflections, and convert the received IR reflections into electrical signals. In one example, controller 100 processes these two electrical signals to determine a biometric. In another example, controller 100 processes these two electrical signals by passing them to a remote processor that determines the biometric.

Biometric sensors 300A and 300B generate the signals simultaneously in the same anatomical region of the user's head, resulting in similar if not identical signals. Controller 100 may use this relationship to either compare or combine the signals. In one example, controller 100 compares the signals for validation. If the comparison indicates that the signals are significantly different, this may indicate that one of the sensors is possibly malfunctioning. In another example, controller 100 compares and combines the signals for accuracy. If the comparison indicates that the signals differ only slightly, the signals may be combined (e.g., averaged together) to produce a more accurate representation of the biometric. In an example where the sensors sense a different biometric, one sensor may sense a first type of biometric parameter (e.g., blood pressure) and another sensor may sense a second type of biometric parameter (e.g., pulse rate).

To reduce power consumption during operation, control electronics 20A (e.g., controller 100) send (e.g., periodically or at the request of the user) an electrical signal to the IR transceiver 300 via the FPCBs rather than continuously applying a signal, which would increase power consumption. For example, the user may initiate the measurement of biometrics by pressing a button on eyewear 12. Controller 100 energizes IR transceiver 300 for defined periods of time and de-energizes IR transceiver 300 for other periods of time. This allows controller 100 to periodically sample the biometric signal of the user while reducing overall power consumption. For example, controller 100 may sample the biometric signal output by sensor 300 at 10-second sampling intervals every 5 minutes. Controller 100 is thereby able to monitor the biometric signal, while conserving battery power.

Figure 5:
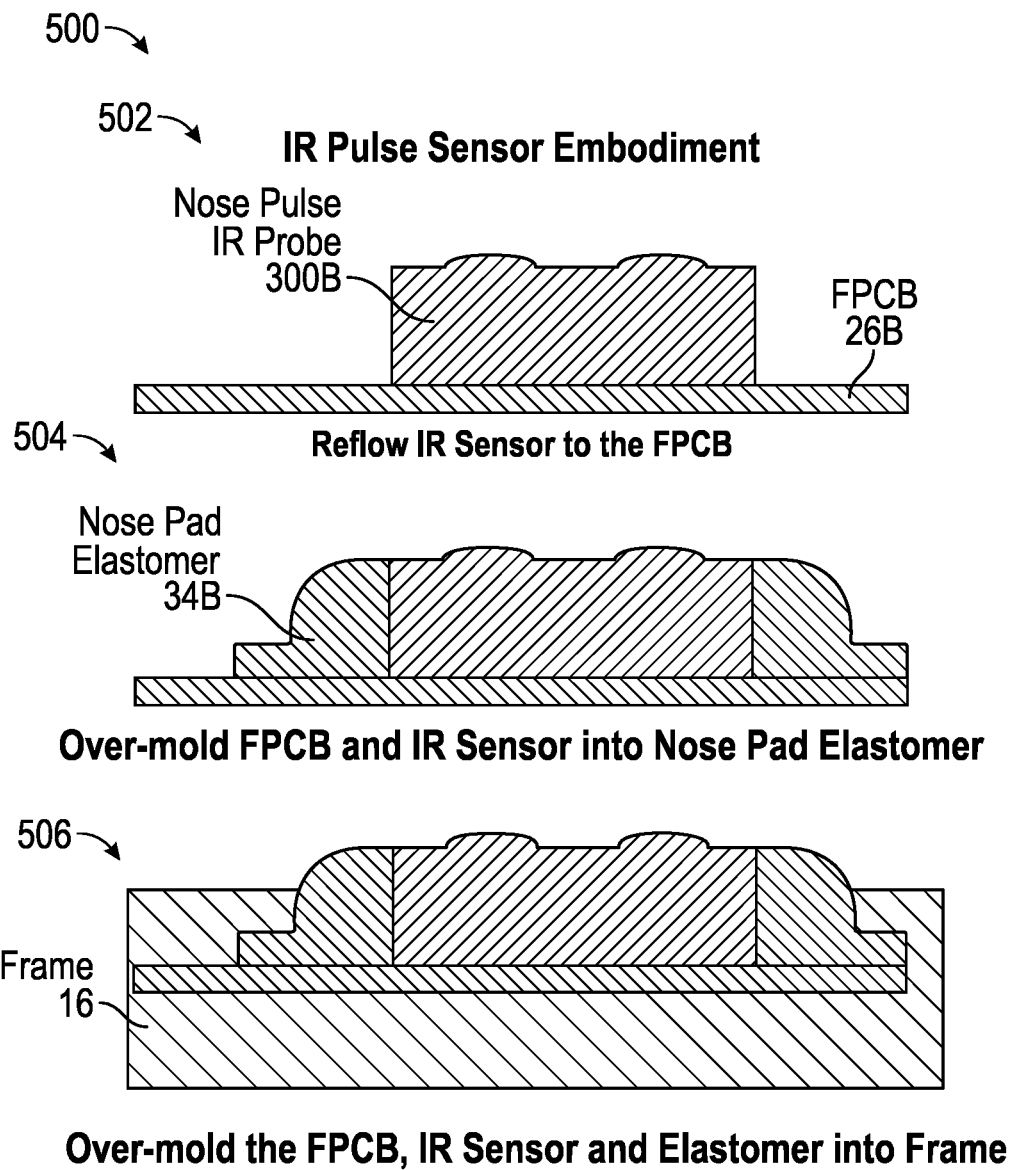
FIG. 5 is a series of illustrations depicting an example of steps for manufacturing eyewear with the biometric sensor in FIG. 3.

FIG. 5 is a series of illustrative example steps 500 depicting manufacture of eyewear 12 with biometric sensor 300B (see FIG. 4B) installed in nose pad 34B (see FIG. 1C). In a first step 502, biometric sensor 300B is mounted (e.g., soldered, adhered, etc.) onto a portion of FPCB 26B. In a second step 504, nose pad nose pad 34B (e.g., elastomer) partially covers biometric sensor 300B. A portion of biometric sensor 300B, however, is still exposed, allowing IR transmitter 304 to transmit the IR light, and allowing IR receiver 302 to receive the reflected IR light. The nose pad may completely cover the biometric sensor 300B, as long as the nose pad is transparent enough that light can pass through. In a third step 506, a molding process (e.g., two-shot molding process) embeds biometric sensor 300B and the nose pad into frame 16.

Figure 6:
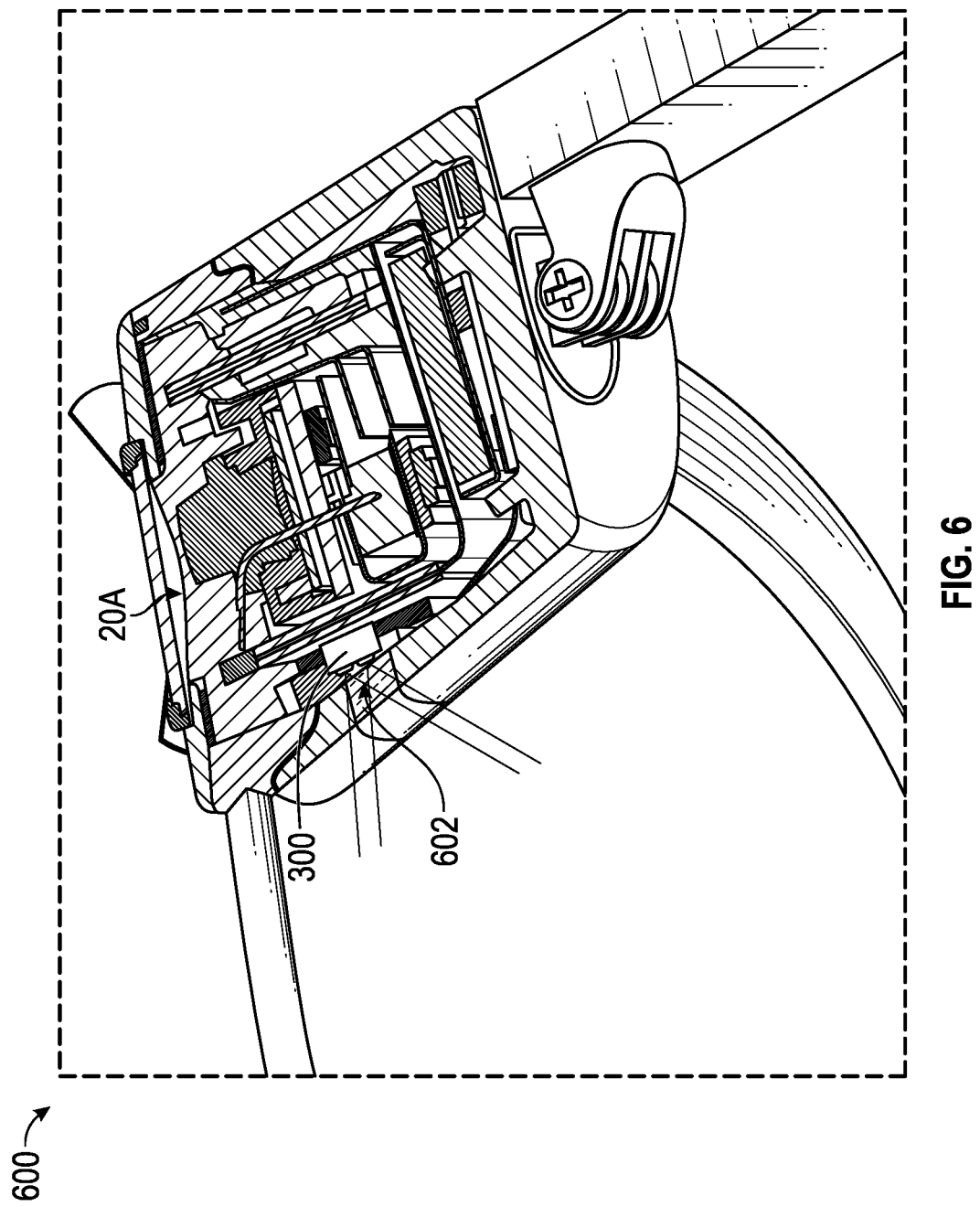
FIG. 6 is an illustration of the biometric sensor in FIG. 3 positioned on the frame of the eyewear example of FIG. 1A.

FIG. 6 depicts a view 600 of biometric sensor (such as IR transceiver 300) embedded into frame 16 at a location where a housing contains electronic components 20A. In this example, biometric sensor 300 mounts to and electrically couples to a PCB within electronic components 20A. The mounting position directs biometric sensor 300 to aim the IR transmitter/receiver towards a region where the user's head is located while wearing eyewear 12. The housing of electronic components 20A may also include an opening or a transparent section 602 that allows the IR light from biometric sensor 300 to enter and exit the housing.

Figure 7:
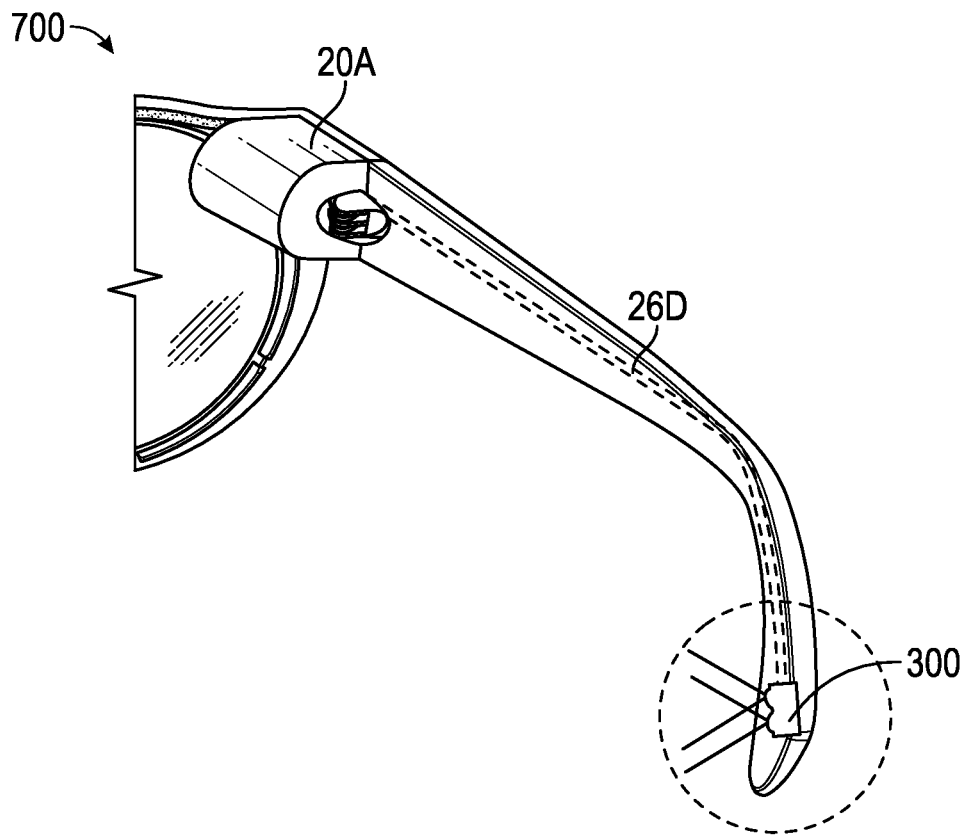
FIG. 7 is another illustration of the biometric sensor in FIG. 3 positioned on the temple of the eyewear example of FIG. 1A.

FIG. 7 depicts a partial view 700 of eyewear 12 including biometric sensor (such as IR transceiver 300) embedded in the temple of eyewear 12 in accordance with another example. FPCB 26D extends from electronic components 20A to biometric sensor 300 located on a portion of temple 14A. Although FIG. 7 depicts biometric sensor 300 mounted at an end of temple 14A, it is also possible to mount biometric sensor 300 at other locations along temple 14A or 14B as long as the mounting location aims biometric sensor 500 in a direction to sense the user's skin when eyewear 12 is worn.

In one example, the electronic components (under control of controller 100) transmit the biometric or signals to a remote processor such as a processor of a portable electronic device (e.g., a smart phone) that computes the biometric based on the signals. An application within the portable electronic device may generate an overlay representing the biometric and make this overlay available for addition to an image gathered concurrently (e.g., within ten seconds) of the biometric.

Various flowcharts now describe further details regarding the operation of eyewear such as eyewear 12.

Figure 8A:
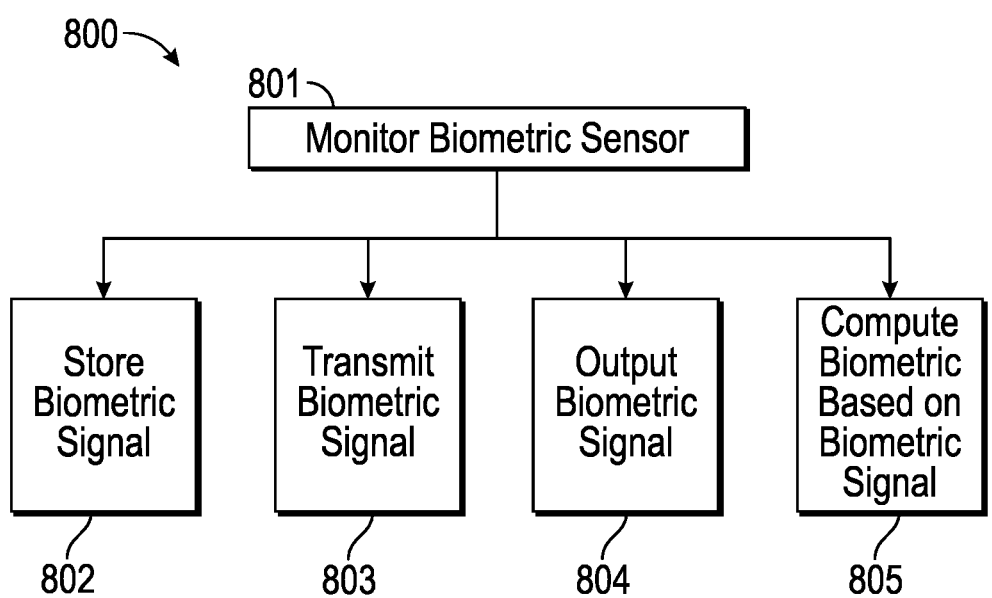
FIG. 8A is a flowchart showing an example of the operation of eyewear having a biometric sensor.

FIG. 8A depicts a flow chart 800 of an example operation of eyewear such as eyewear 12 (FIG. 1A) in which electronic components detect a biometric signal of the user. Controller 100 monitors an electrical signal output by a biometric sensor (e.g., IR sensor 300) in step 801. Controller 100 utilizes this electrical signal in one or more ways, which the following examples illustrate.

In a first example, at step 802, controller 100 stores the biometric signal in internal memory. Later, controller 100 analyzes this stored signal or transmits this stored signal to a personal computing device for further analysis. For example, controller 100 may transmit/download the stored electrical signal to a portable electronic device (e.g., a smartphone) executing a biometric software application.

In a second example, at step 803, rather than storing the signal, controller 100 instructs wireless module 102 to transmit the sensed biometric signal to a personal computing device (e.g., smartphone) for analysis. The personal computing device then computes the biometrics (e.g., heart rate, blood pressure, etc.).

In a third example, at step 804, controller 100 outputs the biometric signal directly to the user. For example, controller 100 displays the user's heart rate to the user by modulating the intensity of an LED visible to the wearer using the electrical signal.

In a fourth example, at step 805, controller 100 computes a biometric of the user based on the signal. For example, controller 100 analyzes the biometric signal to determine heart rate, blood pressure, or some other biometric of the user. Controller 100 then stores the biometric, displays the biometric to the user, or transmits the biometric to a personal computing device.

Although steps 802-805 in FIG. 8A are shown as performed separately, they can be used in various combinations. For example, controller 100 may first store the detected biometric signal, compute a biometric (e.g., heart rate) based on the stored signal, and then transmit the biometric to a portable electronic device for display to the user.

Figure 8B:
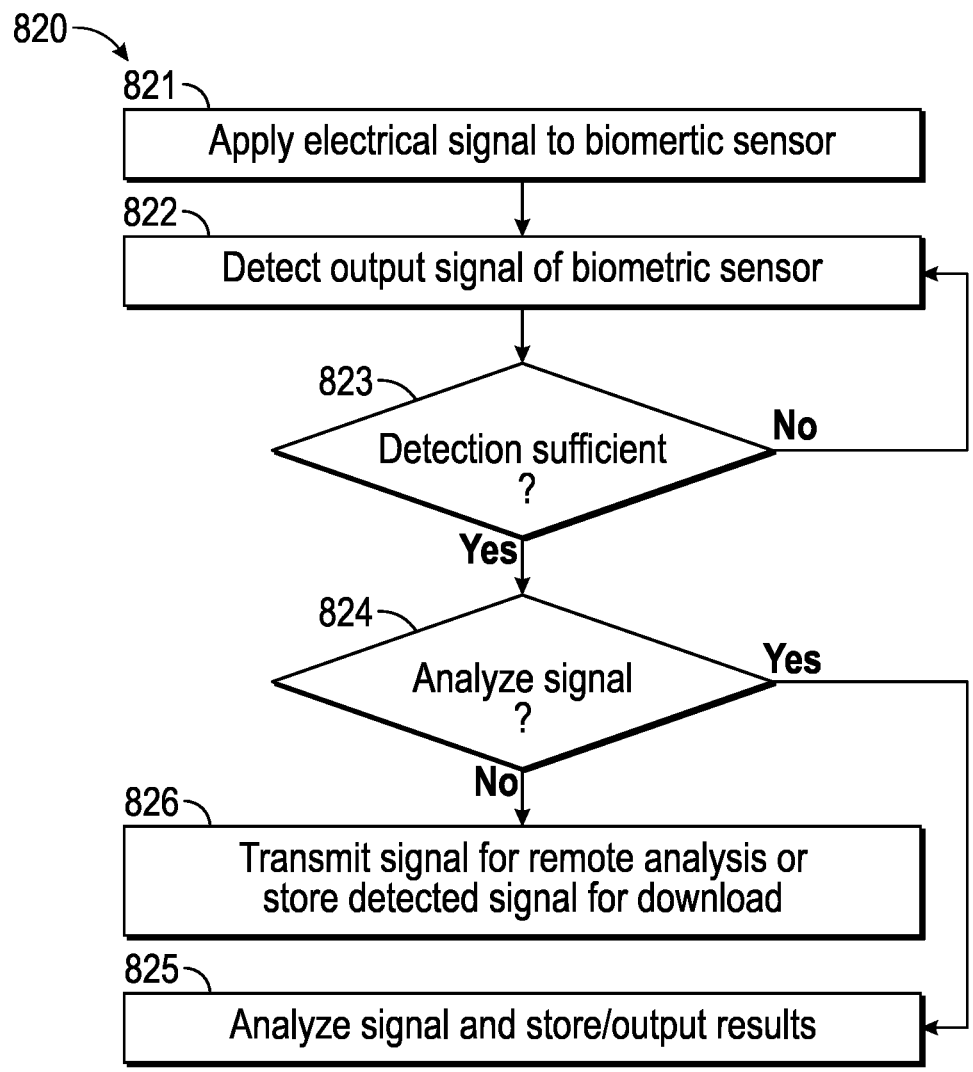
FIG. 8B is a flowchart showing another example of the operation of eyewear having a biometric sensor.

FIG. 8B depicts another flow chart 820 showing further details of example operation of eyewear such as eyewear 12 in which electronic components detect a biometric signal from the user. At step 821, controller 100 applies an electrical signal to the biometric sensor (e.g., IR transceiver 300). Biometric sensor 300 transmits an IR signal and receives a reflection of the IR signal. A detector (e.g., photo-resistor) of biometric sensor 300 then amplitude modulates an electrical signal based on the reflected IR signal.

Controller 100, at step 822, detects the amplitude modulated signal output by biometric sensor 300. Controller 100, at step 823, determines if the detection is sufficient (e.g., enough information is received in the signal) to compute a desired biometric. If controller 100 determines that the signal is not sufficient, controller 100 continues to detect the output of biometric sensor 300. If controller 100 determines that the signal is sufficient, controller 100 determines, at step 824, if it should analyze the signal. For example, controller 100 may read settings (e.g., manufacturer settings, user settings, software developer settings, etc.) to determine if the signal should be analyzed. These settings may be stored in flash memory 106 and may be related to the software application running on eyewear 12 or an external device (e.g., PC, smartphone, etc.). If controller 100 determines (e.g., based on the settings) that it should analyze the signal, controller 100 analyzes the signal at step 825 to determine the biometric. Controller 100 then stores this biometric for later use or for display to the user. For example, the analysis of the signal may be beneficial for outputting the biometric to the user via eyewear 12 (e.g., displaying heartrate variability by blinking an LED on eyewear 12). If controller 100, however, determines (e.g., based on the settings) that it should not analyze the signal, controller 100 either stores the signal in memory for later use, or transmits the signal to a portable electronic device as shown in step 826. The portable electronic device then performs an analysis on the signal. For example, it may be beneficial for an external device (e.g., PC, smartphone, etc.) which has more processing capabilities and/or display options to perform the analysis of the signal and display the biometric results (e.g., the smartphone may receive the biometric signal from eyewear 12, analyze the signal and then display a graphical chart of the biometric results).

Figure 8C:
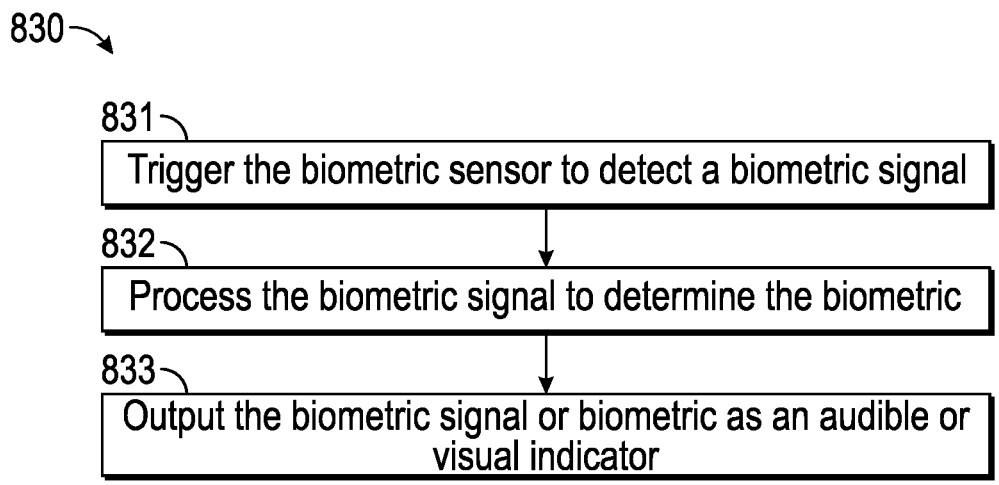
FIG. 8C is a flowchart showing yet another example of the operation of eyewear having a biometric sensor.

FIG. 8C depicts another flow 830 chart showing details of example operation of eyewear such as eyewear 12 in which electronic components detect a biometric signal from the user. At step 831, controller 100 triggers biometric sensor (e.g., IR transceiver 300) to detect a biometric signal. Controller 100 may instruct IR transceiver 300 to emit an IR signal and send a reflective IR signal (modulated with a biometric of the user; a biometric signal) detected by IR transceiver 300. At step 832, controller 100 processes the biometric signal to determine a biometric. Controller 100 may demodulate the biometric signal to recover the biometric modulated onto the biometric signal. At step 833, controller 100 outputs the biometric signal or the biometric to the user using an audible indicator (e.g., via a speaker) or a visual indicator (e.g., via LEDs). For example, if heartrate is the biometric, controller 100 may control the LEDs to flash at the heartrate, or control the speaker to beep at the heartrate.

Although the description and figures of the disclosure focus on the implementation of an infrared (IR) biometric sensor, eyewear 12 may utilize other sensors. In a first example, light sensors that emit and receive light in other bands of the light spectrum may be used. In a second example, the biometric sensor may be an electrode for detecting electrical activity of the user's anatomy. For example, the nose pads, frame, and temple of eyewear 12 provide locations for electrodes to contact the user's skin. Electrical signals detected by these electrodes may then indicate electrical activity (electrophysiological pattern) of the user's heart, brain, facial features, etc. Controller 100 would then store, transmit, or analyze these signals to determine other biometrics.

The steps in FIGS. 8A-8C may be performed by the controller 100 of the electronic components upon loading and executing software code or instructions which are tangibly stored on a tangible computer readable medium, such as on a magnetic medium, e.g., a computer hard drive, an optical medium, e.g., an optical disc, solid-state memory, e.g., flash memory, or other storage media known in the art. Thus, software code or instructions, which are tangibly stored on a tangible computer readable medium, may perform any of the functionality of the controller described herein, such as the steps in FIGS. 8A-8C, may be implemented. Upon loading and executing such software code or instructions by the controller, the controller may perform any of the functionality of the controller described herein, including the steps in FIGS. 8A-8C described herein.

The terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," "includes," "including," or any other variation thereof, are intended to cover a non-exclusive inclusion, such that a process, method, article, or apparatus that comprises or includes a list of elements or steps does not include only those elements or steps but may include other elements or steps not expressly listed or inherent to such process, method, article, or apparatus. An element preceded by "a" or "an" does not, without further constraints, preclude the existence of additional identical elements in the process, method, article, or apparatus that comprises the element.

Unless otherwise stated, any and all measurements, values, ratings, positions, magnitudes, sizes, and other specifications that are set forth in this specification, including in the claims that follow, are approximate, not exact. Such amounts have a reasonable range that is consistent with the functions to which they relate and with what is customary in the art to which they pertain. For example, unless expressly stated otherwise, a parameter value or the like may vary by as much as ±10% from the stated amount.

In addition, the Detailed Description groups various features together in various examples for streamlining the disclosure. This method of disclosure is not to be interpreted as reflecting an intention that the claimed examples require more features than are expressly recited in each claim. Rather, as the following claims reflect, the subject matter to be protected lies in less than all features of any single disclosed example. Thus, the following claims are hereby incorporated into the Detailed Description, with each claim standing on its own as a separately claimed subject matter.

While the foregoing has described what are considered to be the best mode and other examples, it is understood that various modifications may be made therein and that the subject matter disclosed herein may be implemented in various forms and examples, and that they may be applied in numerous applications, only some of which have been described herein. It is intended by the following claims to claim any and all modifications and variations that fall within the true scope of the present concepts.

What is claimed is:

1. Eyewear comprising:
an optical element;
electronic components including a controller and a memory;
a support structure configured to support the optical element and the electronic components, the support structure defining a region for receiving at least a portion of a head of a user; and
first and second biometric sensors coupled to the electronic components and supported by the support structure, the first and second biometric sensors positioned to detect, in the region, first and second biometric signals representative of a same or a different biometric of the user for processing by the electronic components, the biometric including at least one of heart rate, blood pressure, oxygen level in the user's blood, or electrical activity in the user's anatomy, wherein the first biometric sensor includes a first infrared (IR) transmitter and a first IR receiver and the second biometric sensor includes a second IR transmitter and a second IR receiver, and the electronic components are configured to trigger the first and second IR transmitters to periodically transmit first and second IR signals into the region and to receive, at the first and second IR receivers, first and second reflective IR signals that are processed by the electronic components to determine the first and second biometric signals representative of at least one biometric of the user whereby at least one of the first and second IR transmitters and first and second IR receivers are energized and deenergized for defined periods of time during which no biometric signal is detected to reduce power consumption,
wherein when the first and second biometric signals are representative of the same biometric of the user, the first and second biometric signals are generated simultaneously and averaged together to produce a representation of the biometric of the user, and
wherein when the first and second biometric signals are representative of different biometrics of the user, the first biometric signal represents a first biometric parameter and the second biometric signal represents a second biometric parameter.

2. The eyewear of claim 1, wherein the first biometric signal corresponds to a heart rate and the second biometric signal corresponds to a blood pressure of the user wearing the eyewear.

3. The eyewear of claim 1, wherein the support structure comprises:
a frame; and
temples connected to the frame, the temples and frame defining the region for receiving the at least a portion of the head of the user.

4. The eyewear of claim 3, further comprising:
nose pads positioned on the frame, the first and second biometric sensors being positioned within at least one of the nose pads.

5. The eyewear of claim 3, wherein at least one of the first or second biometric sensors is positioned on at least one of the temples at a location adjacent to an ear of the user.

6. The eyewear of claim 1, wherein the controller is configured to analyze the first and second biometric signals to determine the at least one biometric of the user, the electronic components further including an output device configured to output an audible or visual indicator that corresponds to the at least one biometric of the user.

7. The eyewear of claim 1, wherein the memory is configured to record the first and second biometric signals for downloading by a personal computing device.

8. The eyewear of claim 1, wherein the electronic components further comprise a wireless transceiver configured to transmit the first and second biometric signals to a personal computing device.

9. The eyewear of claim 1, wherein the first and second biometric signals are compared by the controller to determine whether the first and second biometric signals are different and whether at least one of the first or second biometric sensors is malfunctioning.

10. The eyewear of claim 1, wherein the controller samples the first and second biometric signals over a predetermined period of time and stores the samples in the memory.

11. An eyewear control method for detecting at least one biometric of a user, the method comprising:
triggering, by electronic components in the eyewear, first and second biometric sensors in the eyewear to detect first and second biometric signals representative of a same or a different biometric of the user, the biometric including at least one of heart rate, blood pressure, oxygen level in the user's blood, or electrical activity in the user's anatomy, by periodically triggering, by the electronic components, the first and second biometric sensors to transmit first and second infrared (IR) signals into a region of the eyewear configured to receive at least a portion of the head of a user and to receive first and second reflective IR signals for analysis to detect at least one biometric signal representative of the at least one biometric of the user whereby at least one of first and second IR transmitters and first and second IR receivers of the first and second biometric sensors are energized and deenergized for defined periods of time during which no biometric signal is detected to reduce power consumption;

and
processing, by the electronic components, the first and second biometric signals to determine the at least one biometric of the user,
wherein when the first and second biometric signals are representative of the same biometric of the user, the first and second biometric signals are generated simultaneously and averaged together to produce a representation of the biometric of the user, and
wherein when the first and second biometric signals are representative of different biometrics of the user, the first biometric signal represents a first biometric parameter and the second biometric signal represents a second biometric parameter.

12. The method of claim 11, further comprising:
transmitting, by a transceiver of the electronic components, the first and second biometric signals to a personal computing device remote from the eyewear.

13. The method of claim 11, further comprising:
outputting, by an audible or visual indicator of the electronic components, the first and second biometric signals to the user wearing the eyewear.

14. The method of claim 11, further comprising sampling, by a controller of the electronic components, the first and second biometric signals over a predetermined period of time and storing the samples in a memory device of the electronic components.

15. The method of claim 11, further comprising comparing, by a controller of the electronic components, the first and second biometric signals to determine whether the first and second biometric signals are different and whether at least one of the first or second biometric sensors is malfunctioning.

16. A non-transitory computer-readable medium storing program code which, when executed, is operative to cause an electronic processor to perform the steps of:
triggering, by electronic components in eyewear, first and second biometric sensors in the eyewear to detect first and second biometric signals representative of a same or a different biometric of a user, the biometric including at least one of heart rate, blood pressure, oxygen level in the user's blood, or electrical activity in the user's anatomy, by periodically triggering, by the electronic components, the first and second biometric sensors to transmit first and second infrared (IR) signals into a region of the eyewear configured to receive at least a portion of the head of a user and receive first and second reflective IR signals for analysis to detect at least one biometric signal representative of the at least one biometric of the user whereby at least one of first and second IR transmitters and first and second IR receivers of the first and second biometric sensors are energized and deenergized for defined periods of time during which no biometric signal is detected to reduce power consumption;
and
processing, by the electronic components, the first and second biometric signals to determine the at least one biometric of the user,
wherein when the first and second biometric signals are representative of the same biometric of the user, the first and second biometric signals are generated simultaneously and averaged together to produce a representation of the biometric of the user, and
wherein when the first and second biometric signals are representative of different biometrics of the user, the first biometric signal represents a first biometric parameter and the second biometric signal represents a second biometric parameter.

17. The computer-readable medium of claim 16, further comprising instructions for implementing functions when executed by the processor of the eyewear, the functions including:
controlling a transceiver of the electronic components to transmit the biometric signal and second biometric signal to a personal computing device remote from the eyewear.

18. The computer-readable medium of claim 16, further comprising instructions for implementing functions when executed by the processor of the eyewear, the functions including:
sampling the first and second biometric signals over a predetermined period of time and storing the samples in a memory device of the electronic components.

19. The computer-readable medium of claim 16, further comprising instructions for implementing functions when executed by the processor of the eyewear, the functions including:
analyzing the first and second biometric signals to determine the at least one biometric of the user, and outputting the first and second biometric signals to the user wearing the eyewear.

20. The computer-readable medium of claim 16, further comprising instructions for implementing functions when executed by the processor of the eyewear, the functions including:
comparing the first and second biometric signals to determine whether the first and second biometric signals are different and whether at least one of the first or second biometric sensors is malfunctioning.

* * * * *